US010585084B2

(12) United States Patent
Levine et al.

(10) Patent No.: US 10,585,084 B2
(45) Date of Patent: Mar. 10, 2020

(54) METHOD AND APPARATUS FOR PERFORMING HEMATOLOGIC ANALYSIS USING AN ARRAY-IMAGING SYSTEM FOR IMAGING AND ANALYSIS OF A CENTRIFUGED ANALYSIS TUBE

(71) Applicants: Joshua D. Levine, Chapel Hill, NC (US); Robert A. Levine, Guilford, CT (US); Stephen C. Wardlaw, Lyme, CT (US); Craig Stout, Port Matilda, PA (US); David A. Clipper, State College, PA (US)

(72) Inventors: Joshua D. Levine, Chapel Hill, NC (US); Robert A. Levine, Guilford, CT (US); Stephen C. Wardlaw, Lyme, CT (US); Craig Stout, Port Matilda, PA (US); David A. Clipper, State College, PA (US)

( * ) Notice: Subject to any disclaimer, the term of this patent is extended or adjusted under 35 U.S.C. 154(b) by 0 days.

(21) Appl. No.: 15/207,074

(22) Filed: Jul. 11, 2016

(65) Prior Publication Data

US 2016/0320369 A1 Nov. 3, 2016

Related U.S. Application Data

(63) Continuation of application No. 13/016,347, filed on Jan. 28, 2011, now abandoned.

(Continued)

(51) Int. Cl.
*G01N 33/49* (2006.01)
*B01L 3/00* (2006.01)
(Continued)

(52) U.S. Cl.
CPC ........ *G01N 33/491* (2013.01); *B01L 3/50215* (2013.01); *B01L 9/065* (2013.01);
(Continued)

(58) Field of Classification Search
CPC .... G01N 33/491; G01N 15/05; G01N 15/042; G01N 2015/045; G01N 2800/22;
(Continued)

(56) References Cited

U.S. PATENT DOCUMENTS 4,027,660 A 6/1977 Wardlaw et al.
4,091,659 A 5/1978 Massey, III et al.
(Continued)

OTHER PUBLICATIONS

Marcus, "Comparison of Methods for Uniform Laser Scanning of Centrifuged Blood Tubes for Data Acquisition in a Hematology Analyzer", IEEE Transactions on Instrumentation and Measurement, vol. 50, No. 6, Dec. 2001.*
Zaitsev et al., ("A Device for Automated Detection and Analysis of Erythrocyte Sedimentation", Biomedical Engineering, vol. 43, No. 3, 2009, pp. 131-134. Translated from Meditsinskaya Tekhnika, vol. 43, No. 3, 2009, pp. 27-32. Original article submitted Jan. 26, 2009).*

(Continued)

*Primary Examiner* — Dean Kwak
(74) *Attorney, Agent, or Firm* — Getz Balich LLC

(57) ABSTRACT

A method and device for analyzing a hematologic sample centrifuged within a capillary tube is provided. The device includes a tube holder, a sample imaging device, a processor, and a sample data display. The sample imaging device is operable to create a digital image of the sample within a region of the tube. The region is defined by substantially all of the radial width and axial length of the sample residing within the internal cavity of the tube in the region where the float resides after centrifugation. The sample imaging device is operable to produce signals representative of the image. The processor is adapted to produce information relating to bands of interest within the image based on the signals from the sample imaging device. The sample data display is adapted to display the results therefrom and/or a digital image of the sample within the region.

8 Claims, 1 Drawing Sheet

Related U.S. Application Data

(60) Provisional application No. 61/351,138, filed on Jun. 3, 2010, provisional application No. 61/305,449, filed on Feb. 17, 2010.

(51) Int. Cl.
   *G01N 15/04* (2006.01)
   *G01N 15/05* (2006.01)
   *B01L 9/06* (2006.01)
   *G06T 7/00* (2017.01)

(52) U.S. Cl.
   CPC ......... *G01N 15/042* (2013.01); *G01N 15/05* (2013.01); *G06T 7/0012* (2013.01); *B01L 2300/027* (2013.01); *B01L 2300/0609* (2013.01); *B01L 2300/0654* (2013.01); *B01L 2300/0838* (2013.01); *G01N 2015/045* (2013.01); *G01N 2800/22* (2013.01); *G06T 2207/30024* (2013.01)

(58) Field of Classification Search
   CPC .... G01N 33/48; G01N 33/5002; G01N 21/07; G01N 21/278; G01N 33/80; G01N 9/12; G01N 2015/055; G01N 33/49; G01N 2015/047; G01N 33/5094; G06T 7/0012; B01L 3/50215; B01L 2300/027; B01L 2300/0609; B01L 2300/0654; B01L 2300/0838; B01L 9/065; B01L 2400/0409; B01L 3/5021; B01L 3/505; B01L 3/561; B04B 5/0414; B04B 13/00; B04B 5/02; B04B 5/0407
   USPC .................. 422/82.05, 415, 546; 436/45
   See application file for complete search history.

(56) References Cited

U.S. PATENT DOCUMENTS

| | | |
|---|---|---|
| 4,137,755 A | 2/1979 | Wardlaw et al. |
| 4,209,226 A | 6/1980 | Wardlaw et al. |
| 4,259,012 A | 3/1981 | Wardlaw |
| 4,558,947 A | 12/1985 | Wardlaw |
| 4,683,579 A | 7/1987 | Wardlaw |
| 5,132,087 A | 7/1992 | Manion et al. |
| 5,888,184 A | 3/1999 | Wardlaw |
| 6,002,474 A | 12/1999 | Thomas et al. |
| 6,197,523 B1 | 3/2001 | Rimm et al. |
| 6,285,450 B1 * | 9/2001 | Thomas ............... B04B 5/0407 356/244 |
| 6,336,358 B1 * | 1/2002 | Kishimori ........... G01N 15/042 73/61.65 |
| 6,441,890 B2 | 8/2002 | Wardlaw |
| 6,444,436 B1 | 9/2002 | Rimm et al. |
| 6,506,606 B1 | 1/2003 | Winkelman et al. |
| 7,499,581 B2 * | 3/2009 | Tribble ................. B65B 3/003 250/577 |
| 7,822,249 B2 | 10/2010 | Garty |
| 2002/0012117 A1 * | 1/2002 | Wardlaw ............. G01N 15/042 356/39 |
| 2008/0179301 A1 | 7/2008 | Garty et al. |
| 2009/0274348 A1 | 11/2009 | Jakubowicz et al. |

OTHER PUBLICATIONS

Zaitsev et al. "A Device for Automated Detection and Analysis of the Erythrocyte Sedimentation", vol. 43, No. 3, 2009, pp. 131-134.
"Accutube User Guide", QBC Autoread Plus, Centrifugal Hematology System, QBC Diagnostics Inc., www. qbcdiagnostics.com.
Office action for EP11706990.6 dated Jun. 21, 2018.
Office action for EP11706990.6 dated Aug. 16, 2019.

* cited by examiner

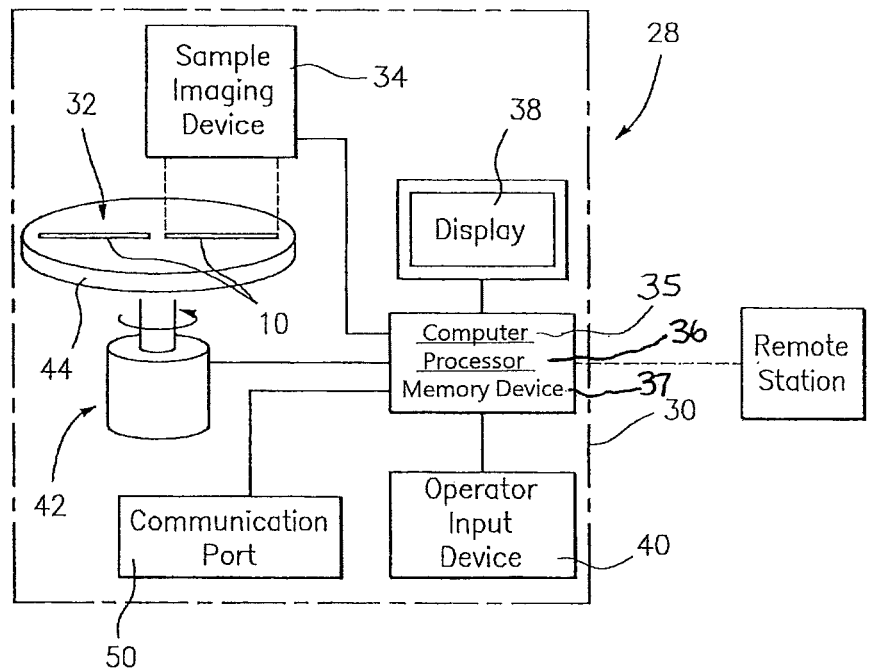
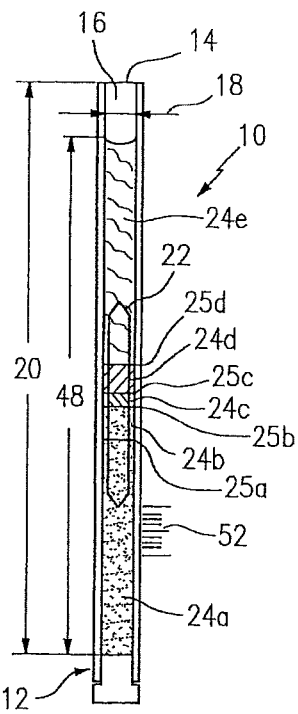
FIG. 2
(PRIOR ART)
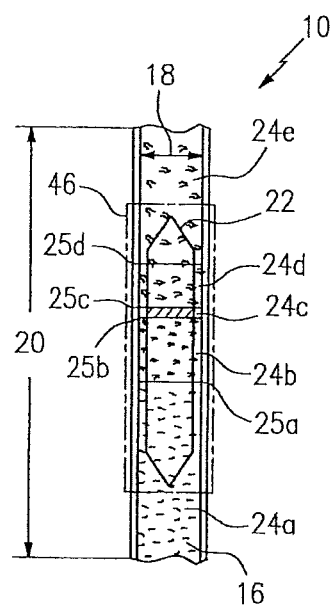
FIG. 3
(PRIOR ART)
FIG. 1

METHOD AND APPARATUS FOR PERFORMING HEMATOLOGIC ANALYSIS USING AN ARRAY-IMAGING SYSTEM FOR IMAGING AND ANALYSIS OF A CENTRIFUGED ANALYSIS TUBE

This application is a continuation of U.S. patent application Ser. No. 13/016,347 filed Jan. 28, 2011, which claims the benefit of U.S. Provisional Patent Application No. 61/305,449 filed Feb. 17, 2010 and U.S. Provisional Patent Application No. 61/351,138 filed Jun. 3, 2010, each of which applications is hereby incorporated by reference in its entirety.

BACKGROUND INFORMATION

U.S. Pat. Nos. 4,027,660; 4,091,659; 4,137,755; 4,209,226; 4,558,947; 4,683,579; 5,132,087; 5,888,184; and 6,441,890 describe methods and apparatus for hematological analysis using a capillary tube and a space occupying insert that floats on the centrifuged red blood cells thereby expanding the surrounding buffy coat and permitting the measurement and quantization of the blood's layers. This method permits the determination of a compete blood count (CBC) consisting of hematocrit, a hemoglobin determination, a total white blood cell count with the latter presented as a total and percent granulocytes and total and percent lymphocytes plus monocytes, as well as a platelet count and a mean red cell hemoglobin concentration. It is widely used through the world for performing point of care CBC in human and veterinary medicine. The device, formerly manufactured and sold by Becton Dickinson, Inc. of New Jersey U.S.A. is now manufactured and sold by QBC Diagnostics, Inc., of Pennsylvania, U.S.A. The apparatus is sold under the trademark of QBC® hematology. The capillary tubes are referred to in the industry as "QBC® tubes".

The QBC® hematology system includes a number of different complex instruments for reading the QBC® tubes, each of which has an illumination system, a power source, an imaging and optical system, a microprocessor, and a display. These devices can cost anywhere from several hundred to many thousands of U.S. dollars. The current versions of both the stand-alone reader and the integral reader-centrifuge (QBC® STAR reader) provide for a linear scan of the tube, either while it is stationary in the case of the stand-alone reader or while the centrifuge is in motion, as is the case with the QBC® STAR reader. In both cases, the linear scan is limited to scanning a single axially extending line scan of the tube, which evaluates only a thin stripe of the area of interest within the tube. Because this method of scanning can only scan a thin stripe of the area of interest at a given time, it is necessary to take multiple axially extending scans taken at different circumferential positions of the tube to determine which of the scans can be used for analytical purposes. By looking at several different scans, each taken at a different circumferential position, it is possible to ascertain whether any particular scan is representative of the sample or if it contains an unrepresentative anomaly. Also, because of the narrow scan, the mechanical and optical alignment of the instrument must be held to a very high tolerance, which also increases the cost of the device.

This is particularly true in the case of the QBC® STAR reader, because the QBC® tube is read while the centrifuge is in motion, necessitating an elaborate timing system to ensure that illumination occurs exactly when the tube is in position under the linear scanning device (e.g., CCD scanner). Another, related problem is the need to provide elaborate vibration damping so that the relative tube and reader position be maintained during this process.

These considerations force the analysis tube readers to have a relatively high price, which limits the market size for the QBC® hematology system because health care providers are reluctant and/or unable to make the requisite equipment investment when the equipment is only used for a few tests per day. In those instances when the point of care giver does not have the analysis equipment, the patient is subjected to the significant inconvenience, harm and expense of having to go to a private laboratory and having to wait often several days to get the result. The lack of an analysis device also makes the physician's job more difficult by precluding immediate results at the point of care. Additionally, regulatory requirements of the United States require that the providers of the test be subject to regulatory supervision under the CLIA (Clinical Laboratory Improvement Act) laws.

What is needed, therefore, is a simple, inexpensive, robust method for reading the centrifuged blood sample at the point of care with immediate availability of results while the health care providers are still with the patient. In addition, a method and device are needed that can provide accuracy results and methodological adherence to proper analytic techniques, as well as quality control measures, particularly those that will permit CLIA waiving, which is subject to less burdensome regulations.

SUMMARY OF THE INVENTION

According to one aspect of the present invention, a device for analyzing a hematologic sample centrifuged within a capillary tube is provided. The tube has an internal compartment with a radial width and an axial length and a float disposed within the tube. The device includes a tube holder, a sample imaging device, a processor, and a sample data display. The sample imaging device is operable to create a digital image of the sample within a region of the tube. The region is defined by substantially all of the radial width and axial length of the sample residing within the internal cavity of the tube in the region where the float resides after centrifugation. The sample imaging device is operable to produce signals representative of the image. The processor is adapted to produce information relating to bands of interest within the image based on the signals from the sample imaging device. The sample data display is adapted to display the results therefrom and/or a digital image of the sample within the region.

According to another aspect of the present invention, a method of analyzing a hematologic sample deposited within a capillary tube is provided. The tube has an internal cavity with a radial width and an axial length, and a float disposed within the tube. The method includes the steps of: a) centrifuging the sample to create constituent bands within the sample disposed in the tube; b) creating an image of a region of the centrifuged sample, which region is defined by substantially all of the radial width and axial length of the sample residing within the internal cavity of the tube in a region where the float resides after centrifugation; c) determining a position for one or more band boundaries using the image; and d) producing analysis results based on the determined band boundaries.

Advantages associated with the present analysis device include the provision of a less expensive, and easier to manufacture, analysis device. The imaging of substantially all of the radial width and a significant portion of the axial length of a centrifuged sample within a capillary tube eliminates many problems associated with narrow linear array sensing. For example, prior art linear array sensing is susceptible to circumferentially located bandwidth anomalies; e.g., if the bandwidth at a particular circumferential position is irregularly too small or too big, data based on that band width will be inaccurate. For this reason, the prior art devices take multiple linear array sensings at non-contiguous circumferential positions and average those sensings, or otherwise compare them to one another for accuracy. The prior art devices, therefore, require hardware that can rotate one or both of the linear sensing array and the sample. The hardware must also be able to provide very accurate mechanical and optical alignment of the instrument relative to the sample, and in the case of a dynamic sensing device like the QBC® STAR reader, also provide elaborate imaging controls and vibration damping. The present device also provides significant quality control mechanisms.

On the other hand, the prior art linear imaging had the advantage of minimal geometric distortion. Since all prior art imaging data was in the form of a narrow linear segment taken at a right angle to the tube as it was scanned, each band position was exactly related to its digital representation. In the case of the image array as used in the present device, in which the tube is positioned some distance from the imaging lens and camera, the bands in the tube are foreshortened in proportion to their distance from the center of the optical axis, and the sides of the tube are particularly affected by this effect, sometimes making them appear crescent shaped. This geometric distortion, in addition to any other distortions from the lens, is preferably accounted for in order to enhance the accuracy of the results. For example, the geometric distortion can be accounted for by using a correction table which accounts for each pixel, or regions in the image. The correction table can be used to re-map the image so that the image positions correctly correspond to the actual locations on the tube surface. This type of correction table can be automatically generated by imaging and analyzing a known 'calibration' standard or if only geometric distortion is involved, the corrections can be simply calculated based on the known distances involved. Alternatively, the geometric distortion can be accounted for by correcting the band lengths following their preliminary measurement.

The foregoing and other objects, features and advantages of the present invention will become more apparent in light of the following drawings and detailed description of the present invention.

BRIEF DESCRIPTION OF THE DRAWINGS

FIG. 1 is a schematic diagram of the present invention hematology analysis device.

FIG. 2 is a schematic diagram of a capillary tube.

FIG. 3 is an enlarged partial view of a tube such as that shown in FIG. 2.

DETAILED DESCRIPTION OF THE INVENTION

Referring to FIGS. 1-3, a blood sample for analysis within the QBC® hematology system is typically obtained either from a venous or capillary sample, centrifuged in a simple, small dedicated centrifuge which may be either battery powered or AC powered. U.S. Pat. Nos. 4,027,660; 4,683,579 and 6,441,890, each of which is hereby incorporated by reference in its entirety, describe methods and apparatus for hematological analysis using a capillary tube and a space occupying insert that floats on the centrifuged red blood cells thereby expanding the surrounding buffy coat and permitting the measurement and quantization of the blood's layers. The capillary tube 10 includes a body that extends between a closed bottom 12 and an open top 14. In some embodiments, the "closed bottom" may be vented to allow the escape of gas. The open top 14 provides access to an internal cavity 16 that has a radial width 18 and an axially extending length 20. In those embodiments where the tube 10 is cylindrical, the radial width 18 is the inner diameter of the tube 10. The present invention is not limited to use with any particular type of capillary tube. U.S. Pat. No. 4,027,660, for example, describes a QBC® style capillary tube operable to contain a fluid sample and a volume occupying mass 22 (hereinafter referred to as a "float"), and the information available by virtue of the relative positioning of the float 22 within the sample after centrifugation. The outer diameter of the float 22 is sufficiently smaller than the radial width 18 of the internal cavity 16 so that the float 22 is slidable within the internal cavity 16 and can move axially within the internal cavity 16 during centrifugation of the blood sample. U.S. Pat. No. 6,444,436 describes a different style of capillary tube that can be used with the present invention; e.g., one having a polynomial (e.g., rectilinear) cross-sectional geometry. FIGS. 2 and 3 of the present application diagrammatically illustrate a capillary tube 10 with a sample and a float 22 disposed in the internal cavity 16 of the tube 10. The centrifuged sample disposed in the tube 10 illustrates the constituent bands 24 (24a, 24b, 24c, 24d, 24e) and the band boundaries 25 (25a, 25b, 25c, 25d) therebetween. U.S. Pat. Nos. 4,683,579 and 6,441,890 describe automated devices for reading the centrifuged sample by way of an axially extending linear scan of a limited portion of the sample disposed within the QBC® tube, which limited linear portion is disposed at a particular circumferential position of the tube 10. In the embodiment shown in FIG. 1, the mass 6 takes the form of a right cylindrical insert or plug which is composed of a material having a predetermined specific gravity which renders the mass buoyant upon the centrifuged red cell mass. Due to its shape, the insert 6 will be held in the tube bore 4 so that both have substantially coincidental axes at all times. The diameter of the insert 6 is sufficiently smaller than the diameter of the tube bore 4 so as to be slidable within the tube bore 4 so that the insert 6 can gravitate to the red cell layer during centrifugation of the blood sample and float upon the red cell layer after centrifugation.

The present invention analysis device operates with a capillary tube 10 such as those provided within a QBC® hematology system; i.e., a tube 10 filled with a sample that has been centrifuged to produce the separated constituent layers (i.e., "bands") 24 within the sample. One embodiment of the present analysis device 28 includes a housing 30 containing a tube holder 32, a sample imaging device 34, a computer 35 having a processor 36 and a non-transitory memory device 37, which processor 36 is adapted to produce information relating to bands 24 of interest within the image based on the signals from the sample imaging device 34, a sample data display 38, and may include an operator input device 40 that enables the operator to enter relevant patient information.

In some embodiments, the analysis device 28 further includes a centrifuge 42 with a platen 44 configured to hold one or more capillary tubes 10 in a position where the tubes 10 extend radially outward from a central axis. In these embodiments, the analysis device 28 can perform both the centrifugation and the image analysis. The centrifuge 42 is operable to centrifugally spin the tube 10 containing the sample about the central axis at speeds sufficient to create constituent layer separation within the sample disposed in the tube 10. In these embodiments, the platen 44 is an example of a tube holder 32. In other embodiments, the tube holder 32 may be independent of the centrifuge 42.

The sample imaging device 34 includes a digital camera operable to image substantially all of the radial width 18 and axial length 20 of the sample residing within the internal cavity 16 of the tube 10 in the region 46 (see FIG. 3) where the float 22 resides after centrifugation in a single image, and to produce signals representative of the image. In the preferred embodiments, the sample imaging device 34 is operable to image a region 48 comprising substantially all of the radial width 18 and axial length 20 of the sample within the tube 10 in a single image, and to produce signals representative of the image. Alternately, two or more cameras can be used to image separate portions of the tube 10, which portions are contiguous with one another. The images of the contiguous regions can be subsequently combined and analyzed or are separately analyzed. Either the digital camera itself, or an independent light source within the sample imaging device 34, provides sufficient lighting so that bands 24 of interest within the centrifuged sample may be differentiated within the sample image. The optical resolution of the camera must be sufficient to provide adequate clarity within the image for the analysis at hand; e.g., to differentiate bands 24 of interest. As indicated above, the sample imaging device 34 may be incorporated into a QBC® tube type reader, or may be an independent device (e.g., a portable digital camera, a cell phone camera, etc.) configured for use with such a reader. An example of an acceptable digital camera is a Bayer-type matrix color camera. If, for example, a standard Aptina® five megapixel color camera chip with a frame width of 2592 pixels is used, it can produce a theoretical image resolution of 0.02 mm, which is acceptable for most analyses. If a color camera is used, color filters and different illumination types are likely not required. A grey scaled camera may also be used because the separated buffy coat layers have different light scattering properties and may therefore be detected using a black and white camera, although this measurement is less robust and requires more controlled illumination. The sample imaging device 34 may be described as an "area-array imaging device" because it images substantially all of the radial width 18 and axial length 20 of the sample within the interior cavity 16. If a plurality of cameras is used within the present sample imaging device 34, the images they produce are contiguous with one another thereby permitting the plurality of images to be combined into a single representative image. The linear scan devices of the prior art, in contrast, are limited to producing narrow linear segments that do not extend across the full radial width 18, and the circumferential linear segments are not contiguous with each other. As a result, the circumferentially positioned linear segments cannot be combined into a single representative image. Examples of acceptable independent light sources include white and/or blue LEDs, operable either in a steady state mode or in the case of the QBC® STAR type reader, in a pulsed mode. The relative blue spectrum of a white LED or the inclusion of a separate blue LED can excite the fluorescence of a dye such as Acridine Orange in the tube 10.

The processor 36 is adapted (e.g., programmed) to perform several tasks. Specifically, the processor 36 is in communication with the non-transitory memory device 37 that stores instructions, which instructions when executed by the processor 36 cause the processor 36 to selectively perform tasks, including: a) controlling the sample imaging device 34 based on the analysis at hand; b) controlling the centrifuge 42 for those embodiments that include one; c) receiving and acting on operator input entered through the operator input device 40; and d) producing information relating to bands 24 of interest within the image based on the signals from the sample imaging device 34. The extent of the information relating to the bands 24 can vary depending upon the embodiment of the device 28. For example, the processor 36, when executing the stored instructions, may provide information relating to the adequacy of the sample image, and/or with algorithmic capability that is operable to analyze the signals representative of the sample image and produce data (e.g., CBC, hematocrit, WBC count, etc.) relating thereto based on characteristics of the different bands 24 within the centrifuged sample. In some applications, the processor 36, when executing the stored instructions, can produce graphic markings based on the analysis of the sample that can be superimposed over the sample image when displayed to illustrate the calculated band boundaries 25 relative to the sample image. Using the analysis of a blood sample as an example, graphic markings can be used to identify features such as the: a) bottom of the tube 10; b) bottom of the float 22; c) red blood cell/granulocyte interphase; d) granulocyte/lymphocyte and monocyte interphase; e) lymphocyte and monocyte/platelet interphase; f) platelet/plasma interphase; g) top of the float 22; h) plasma/air interphase; etc.

The sample data display 38 is in communication with the processor 36 and includes a display screen. The display screen is an electronic screen (e.g., flat screen LED, LCD, etc.) operable to display the calculated results and/or a digital image of the sample residing within the centrifuged sample with sufficient optical resolution so that the image can be evaluated by a technician operator to provide the information pertaining to the bands 24 of interest within the centrifuged sample. In those embodiments that include an operator input device 40 (e.g., key pad, touch screen, etc.), the operator input device 40 allows the operator to enter relevant patient or other information, if desired. The sample display 38 may be integral with the housing 30, or it may be an independent device in communication with the processor 36. For example, universal monitors are often used in medical facilities, which monitors have the capability of displaying data from more than one analysis device. In such an application, the data to be displayed may be viewed on an integral display screen and/or a remotely located display device in communication with the processor 36.

In some embodiments, the analysis device 28 includes a communication port 50 for sending the signals representative of the sample image to a remote location. The communication port 50 can be a hardwire port for communicating by hardwire connection to a remote site, or it can be a wireless communication connection (e.g., similar to that used in a wireless phone).

In some embodiments, fiduciary marks 52 (i.e., calibration, measurement marks, etc.) may be placed on or in the capillary tube 10, or the tube holder 32, or on a measuring device positioned adjacent the tube 10 (e.g., a ruler) to facilitate geometric and/or optical calibration and thereby account for any image distortion introduced by the camera. In those instances where the fiduciary marks are placed on or in the tube, a particularly useful embodiment is one wherein the marks are positioned relative to the internal cavity to permit geometric evaluation of sample within the internal cavity. In those instances where fiduciary marks 52 are disposed on a measuring device positioned adjacent the tube 10, the measurement device can measure along an axis that is maintained parallel to the lengthwise axis (e.g., axial direction) of the tube 10. In such embodiments, the measurement device is preferably in close proximity (e.g., in the same focal plane) as the sample tube 10. Alternately, a look-up-table can be provided by factory calibration to serve this function. During the image processing and analysis steps, the calibration information can be used to ensure correct length measurements of the tube 10 features, regardless of their position in the image frame or distance from the camera and can compensate for instrument-to-instrument differences.

Operation:

A fluid sample (e.g., whole blood) is collected from a patient and deposited into a capillary tube 10 such as those used in the QBC® hematology system for subsequent centrifugation. As indicated above, the centrifuge may be independent of, or incorporated into, the analysis device 28. The sample is centrifuged for a period of time adequate to create constituent layer separation within the sample disposed in the tube 10, and the representative bands 24 associated therewith. The centrifuged sample is then imaged using the sample imaging device 34. The image includes substantially all of the radial width 18 and axial length 20 of the sample residing within the internal cavity 16 of the tube 10 in the region where the float 22 resides after centrifugation. Because capillary tubes 10 are not always filled with the exact same volume of fluid sample, the sample imaging device 34 preferably images the region 48 of the tube 10 from the top meniscus to the bottom of the red blood cell layer. It is desirable, but not required, that the bottom of the tube 10 be imaged as well. If the sample being imaged is disposed within a STAR type QBC® tube, for example, the total length between the tube bottom to the tube top fill position is approximately 53 mm. The distance from the tube top fill position to the bottom of the float 22 in most instances is about 37 mm. In those device 28 embodiments that include a centrifuge, the sample may be centrifuged and the centrifuge subsequently stopped or slowed to a very low RPM prior to the imaging. The sample imaging device 34 produces signals representative of each image and communicates those signals to the processor 36.

The images signals are subsequently analyzed within the processor 36 using image processing algorithms provided within the stored instructions to isolate and analyze the bands 24 of interest within the sample, and in some instances relevant sections of the bands 24. Before or after the image signals are analyzed, the image signals may be sent to the sample data display 38 for evaluation by the operator. The ability to have an operator visually evaluate an image that includes substantially all of the radial width 18 of the sample within the tube 10, and a relevant portion of the axial length 20 of the sample is a substantial advancement of the technology. A person of skill in the art will recognize that no automated system can account for all potential variables within the sample image. For example, during the centrifugation process, there is a chance that sample will exit the capillary tube 10 and pass into the retaining tube of the centrifuge. In such instances, the released sample can contaminate the exterior of the capillary tube 10 and inhibit accurate analysis. Similarly, a misplaced tube label or debris deposited on the exterior of the capillary tube 10 during handling can also inhibit or prevent accurate analysis. In these instances, the ability of the present device 28 to produce a single substantially complete image of the centrifuged sample will enable the operator to identify such potential problems and take appropriate action. As another example, the image available with the present device 28 will also enable the operator to evaluate other aspects of the sample image for potential problems; e.g., overall image quality, accuracy of sample coloration, the degree to which a blood sample may be lipemic or icteric, etc. In those applications where the operator evaluates the image after processing and boundary markings are assigned by the processor 36, the operator can evaluate whether the assigned boundary markings are accurately positioned relative to the sample image. Hence, the ability to have an operator visually evaluate an image using the present device 28 provides considerable quality controls to the analysis process. It should be emphasized that the present instrument, as described herein, may be used in locations where trained operators are present, and also locations where no trained operators are present (e.g., a CLIA-waived environment). In the latter type location, the sample images captured by the present device 28 may be sent to a remotely located trained operator for analysis. If it is not possible to have a trained operator review the image and/or results within a predetermined period of time, the present device 28 may be programmed to prevent the release of any data if the sample image has any detectable anomalies. A visual image analysis is preferable in that the criteria for analysis rejection can be loosened, but a purely automated analysis (e.g., that checks for anomalies) is preferable to no analysis at all.

The extent to which the present device 28 images the centrifuged sample within the tube 10 makes possible another quality control mechanism. As indicated above, the present device 28 images substantially all of the radial width 18 and a significant portion of the axial length of the centrifuged sample. In some instances, the radial portion of the image can be expanded to a point outside of the capillary tube 10 to include other imageable features such as calibration markers or areas. The image characteristics associated with the regions outside of the capillary tube 10 can be compared against the characteristics of the region inside the tube 10. Inconsistencies identified by the comparison of the characteristics (e.g., brightness) can be used to evaluate the accuracy of the image. This type of quality control is not possible using the prior art reading devices that utilize a linear scanning device, which has essentially only a one pixel width.

Although the invention has been described and illustrated with respect to exemplary embodiments thereof, the foregoing and various other additions and omissions may be made therein and thereto without departing from the spirit and scope of the present invention.

What is claimed is:

1. An apparatus for analyzing a hematologic sample disposed within a capillary tube, the apparatus comprising:
　at least one capillary tube, which tube extends axially between a top end and a bottom end, and includes an axially extending internal compartment with a radial width and an axial length, and a float disposed within the internal compartment, said float is configured to be axially slidable within the internal compartment;
　a tube holder that is a platen portion of a centrifuge, which platen is rotatable about a central axis, and which platen is configured to hold at least one capillary tube in a position where the at least one capillary tube extends radially outward from the central axis;
　a sample imaging device including a digital imaging camera;
　a sample data display; and
　a computer having a processor and a non-transitory memory device, said processor in communication with at least the non-transitory memory device, the sample imaging device, and the sample data display, and said non-transitory memory device storing instructions that when executed by the processor, cause the processor to:
control the sample imaging device to create a digital image of a sample region, the sample region extending across all of the radial width and axial length of the internal compartment of the tube in a region of the internal compartment of the tube including where the float resides, and to produce signals representative of the image;
produce hematologic information based on the signals from the sample imaging device; and
control the sample data display to display the hematologic information.

2. The apparatus of claim 1, further comprising a communication port.

3. The apparatus of claim 1, wherein the instructions stored within the non-transitory memory device when executed by the processor, cause the processor to control the centrifuge to centrifugally spin the at least one capillary tube containing sample about the central axis at speeds sufficient to create constituent layer separation within the sample disposed in the at least one capillary tube.

4. The apparatus of claim 1, wherein the instructions stored within the non-transitory memory device when executed by the processor, cause the processor to control the sample data display to display the digital image of the sample region.

5. The apparatus of claim 4, wherein the instructions stored within the non-transitory memory device when executed by the processor, cause the processor to control the sample data display to display superimposed graphic markings based on an analysis of the sample over the digital image to illustrate band boundaries.

6. The apparatus of claim 5, wherein the graphic markings are superimposed to identify at least one of a bottom of the tube, a bottom of the float, a red blood cell/granulocyte interphase, a granulocyte/lymphocyte and monocyte interphase, a lymphocyte and monocyte/platelet interphase, a platelet/plasma interphase, a top of the float, or a plasma/air interphase.

7. The apparatus of claim 1, wherein the information relating to the image based on the signals from the sample imaging device includes complete blood count information.

8. An apparatus for analyzing a hematologic sample disposed within a capillary tube, the apparatus comprising:
at least one capillary tube, which tube extends axially between a top end and a bottom end, and includes an axially extending internal compartment with a radial width and an axial length, and a float disposed within the internal compartment, said float is configured to be axially slidable within the internal compartment;
a tube holder that is a platen portion of a centrifuge, which platen is rotatable about a central axis, and which platen is configured to hold at least one capillary tube in a position where the at least one capillary tube extends radially outward from the central axis;
a sample imaging device, the device including a digital camera; and
a computer having a processor and a non-transitory memory device, said processor in communication with at least the non-transitory memory device and the sample imaging device, and said non-transitory memory device storing instructions that when executed by the processor, cause the processor to:
control the sample imaging device to create a digital image of a sample region, the sample region extending across all of the radial width and axial length of the internal compartment of the tube in a region of the internal compartment of the tube including where the float resides, and to produce signals representative of the image;
produce hematologic information based on the signals from the sample imaging device.

* * * * *